United States Patent [19]

Klein et al.

[11] Patent Number: 5,536,250
[45] Date of Patent: Jul. 16, 1996

[54] PERFUSION SHUNT DEVICE AND METHOD

[75] Inventors: Enrique J. Klein; Paul M. Goeld, both of Los Altos, Calif.

[73] Assignee: Localmed, Inc., Palo Alto, Calif.

[21] Appl. No.: 305,250

[22] Filed: Sep. 13, 1994

Related U.S. Application Data

[63] Continuation-in-part of Ser. No. 221,613, Apr. 1, 1994.

[51] Int. Cl.⁶ .................................................. A61M 29/00
[52] U.S. Cl. .......................... 604/96; 604/102; 604/264; 604/53
[58] Field of Search ................................ 604/96, 21, 53, 604/104, 97, 103, 52, 107, 49, 28, 266, 264, 101; 606/108, 192, 194; 623/1

[56] References Cited

U.S. PATENT DOCUMENTS

| | | |
|---|---|---|
| 3,173,418 | 3/1965 | Baran . |
| 3,394,705 | 7/1968 | Abramson . |
| 3,938,502 | 2/1976 | Bom . |
| 4,292,974 | 10/1981 | Fogarty et al. . |
| 4,323,071 | 4/1982 | Simpson et al. . |
| 4,327,721 | 5/1982 | Goldin et al. . |
| 4,406,656 | 9/1983 | Hattler et al. . |
| 4,417,576 | 11/1983 | Baran . |
| 4,437,856 | 3/1984 | Valli . |
| 4,576,177 | 3/1986 | Webster, Jr. . |
| 4,661,094 | 4/1987 | Simpson . |

(List continued on next page.)

FOREIGN PATENT DOCUMENTS

| | | |
|---|---|---|
| WO92/11890 | 7/1992 | WIPO . |
| WO92/11895 | 7/1992 | WIPO . |
| 9321985 | 11/1993 | WIPO . |
| WO93/21985 | 11/1993 | WIPO . |
| 9411048 | 5/1994 | WIPO . |
| 9411053 | 5/1994 | WIPO . |
| WO94/11048 | 5/1994 | WIPO . |
| WO94/11053 | 5/1994 | WIPO . |
| WO95/03082 | 2/1995 | WIPO . |

OTHER PUBLICATIONS

ACS Rx Perfusion™ Coronary Dilatation Catheter, Advanced Cardiovascular Sys., Inc., Temecula, CA 1990. (package insert).
Bom, N. et al. "Early and recent intraluminal ultrasound devices," 1989, Internal Journal of Cardiac Imaging 4:79–88.
Advanced Cardiovascular Systems, Inc., Temecula, California, "ACS Rx Perfusion™ Coronary Dilatation Catheter," 1990, (Product Brochure) pp. 1–23.
Hong, M. K. et al. "A New PTCA Balloon Catheter With Intramural Channels For Local Delivery of Drugs at Low Pressure," 1992, Supplement to Circulation, Abstracts From the 65th Scientific Sessions, vol. 86, No. 4, #1514.
EndoSonics, Pleasanton, California, "The Cathscanner® Intracoronary Imaging System," 1992, (Product Brochure).
SCIMED®, Maple Grove, Minnesota, "Dispatch™," 1994, (Product Brochure).

*Primary Examiner*—C. Fred Rosenbaum
*Assistant Examiner*—Perry E. Van Over
*Attorney, Agent, or Firm*—Townsend and Townsend and Crew

[57] ABSTRACT

A perfusion shunt device is used in conjunction with balloon catheters to provide blood perfusion across an inflated balloon in a blood vessel. The perfusion shunt device comprises a flexible conduit structure having one or more blood perfusion paths formed from a proximal end to a distal end thereof. The flexible conduit structure is usually attached directly or indirectly to a proximal shaft structure. Discrete anchors or expansible sleeves or cages are provided for locating the conduit structure over the balloon on the catheter. The flexible conduit structure will not be directly attached to the balloon, but rather will be secured at locations distal to an proximal of the balloon. In this way, constriction and distortion of the conduit structure and/or balloon resulting from balloon expansion are minimized. The device may be loaded over a conventional angioplasty balloon catheter within or outside of the blood vessel being treated, either before or after an angioplasty procedure.

21 Claims, 6 Drawing Sheets

U.S. PATENT DOCUMENTS

| | | |
|---|---|---|
| 4,681,564 | 7/1987 | Landreneau . |
| 4,693,243 | 9/1987 | Buras . |
| 4,744,790 | 5/1988 | Jankowski et al. . |
| 4,762,129 | 8/1988 | Bonzel . |
| 4,775,371 | 10/1988 | Mueller, Jr. . |
| 4,776,337 | 10/1988 | Palmaz . |
| 4,790,315 | 12/1988 | Mueller, Jr. et al. . |
| 4,841,977 | 6/1989 | Griffith et al. . |
| 4,850,358 | 7/1989 | Millar . |
| 4,850,969 | 7/1989 | Jackson . |
| 4,877,031 | 10/1989 | Conway et al. .................. 128/344 |
| 4,911,163 | 3/1990 | Fina ................................. 606/127 |
| 4,917,097 | 4/1990 | Proudian et al. ............. 128/662.06 |
| 4,950,232 | 9/1990 | Ruzicka et al. .................... 604/43 |
| 4,976,689 | 12/1990 | Buchbinder et al. ............... 604/95 |
| 4,994,033 | 2/1991 | Shockey et al. .................. 604/101 |
| 5,000,734 | 3/1991 | Boussignac et al. ............... 604/96 |
| 5,007,897 | 4/1991 | Kalb et al. ......................... 604/43 |
| 5,009,636 | 4/1991 | Wortley et al. ..................... 604/43 |
| 5,015,232 | 5/1991 | Maglinte ............................ 604/96 |
| 5,019,042 | 5/1991 | Sahota ............................. 604/101 |
| 5,021,044 | 6/1991 | Sharkawy ........................... 604/53 |
| 5,034,001 | 7/1991 | Garrison et al. ................... 604/53 |
| 5,041,089 | 8/1991 | Mueller et al. ..................... 604/96 |
| 5,046,497 | 9/1991 | Millar ............................... 128/637 |
| 5,049,132 | 9/1991 | Shaffer et al. .................... 604/101 |
| 5,087,244 | 2/1992 | Wolinsky et al. ................... 604/53 |
| 5,087,247 | 2/1992 | Horn et al. ........................ 606/192 |
| 5,092,877 | 3/1992 | Pinchuk ............................... 623/1 |
| 5,102,390 | 4/1992 | Crittenden et al. ................ 604/96 |
| 5,102,415 | 4/1992 | Guenther et al. . |
| 5,112,305 | 5/1992 | Barath et al. . |
| 5,117,831 | 6/1992 | Jang et al. . |
| 5,163,921 | 11/1992 | Feiring . |
| 5,180,364 | 1/1993 | Ginsburg . |
| 5,180,366 | 1/1993 | Woods . |
| 5,180,368 | 1/1993 | Garrison . |
| 5,192,307 | 3/1993 | Wall . |
| 5,203,338 | 3/1993 | Jang . |
| 5,213,576 | 5/1993 | Abiuso et al. . |
| 5,219,326 | 6/1993 | Hattler . |
| 5,219,335 | 6/1993 | Willard et al. . |
| 5,226,888 | 7/1993 | Arney . |
| 5,242,396 | 9/1993 | Evard . |
| 5,254,089 | 10/1993 | Wang . |
| 5,257,974 | 11/1993 | Cox ..................................... 604/96 |
| 5,266,073 | 11/1993 | Wall . |
| 5,281,200 | 1/1994 | Corso, Jr. et al. . |
| 5,282,785 | 2/1994 | Shapland et al. . |
| 5,284,473 | 2/1994 | Calabria . |
| 5,295,962 | 3/1994 | Crocker et al. . |
| 5,300,085 | 4/1994 | Yock . |
| 5,306,250 | 4/1994 | March et al. . |
| 5,308,356 | 5/1994 | Blackshear, Jr. et al. . |
| 5,318,535 | 6/1994 | Miraki . |
| 5,344,401 | 9/1994 | Radisch et al. . |
| 5,358,487 | 10/1994 | Miller . |
| 5,364,356 | 11/1994 | Höfling . |
| 5,370,617 | 12/1994 | Sahota . |
| 5,378,237 | 1/1995 | Boussignac et al. . |
| 5,395,333 | 3/1995 | Brill . |
| 5,415,637 | 5/1995 | Khosravi . |
| 5,425,709 | 6/1995 | Gambale . |
| 5,433,706 | 7/1995 | Abiuso . |
| 5,439,445 | 8/1995 | Kontos ................................ 604/96 |

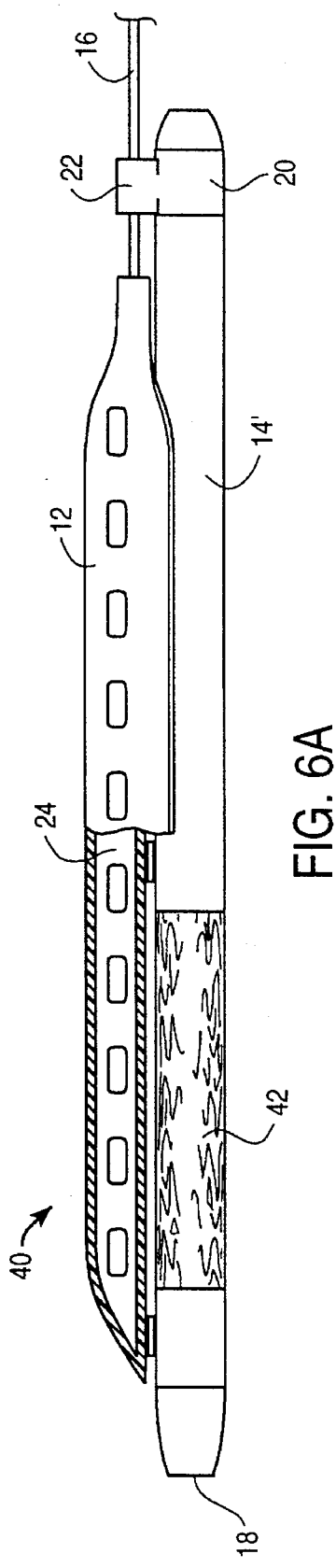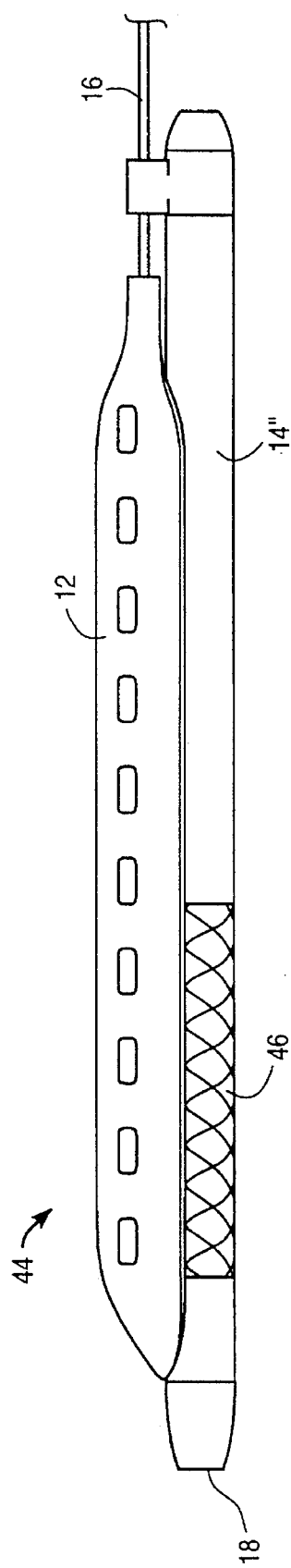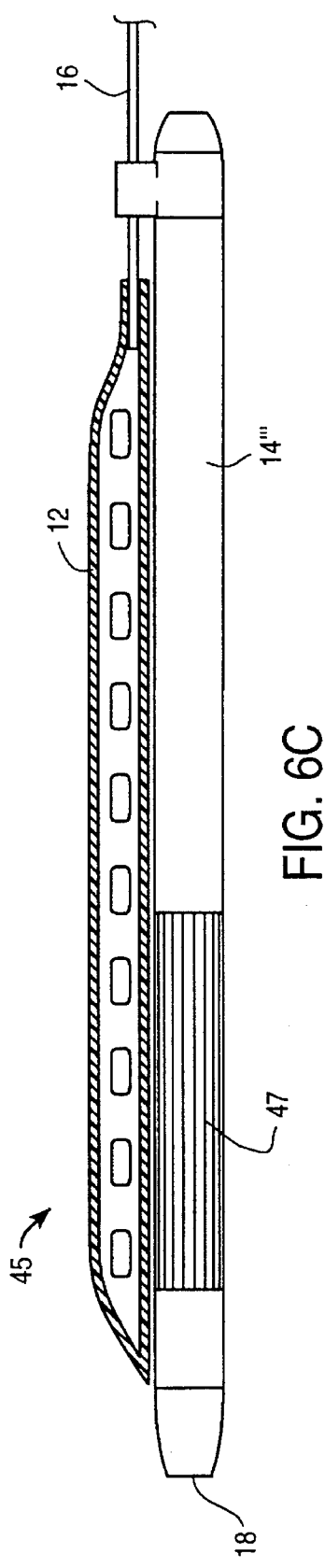

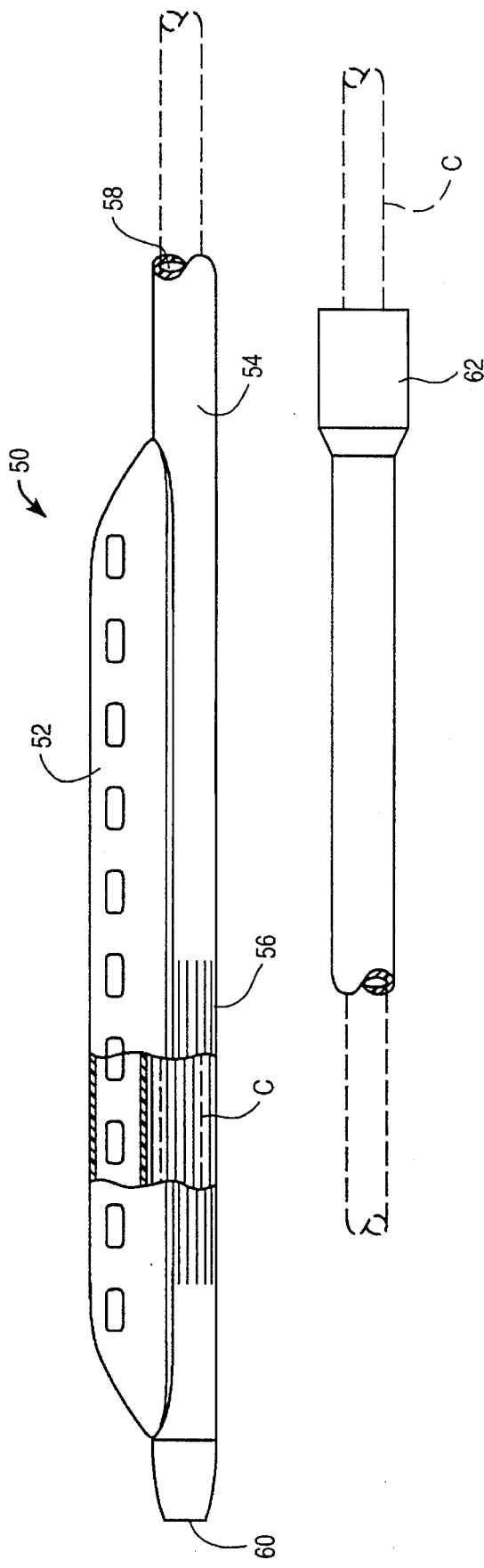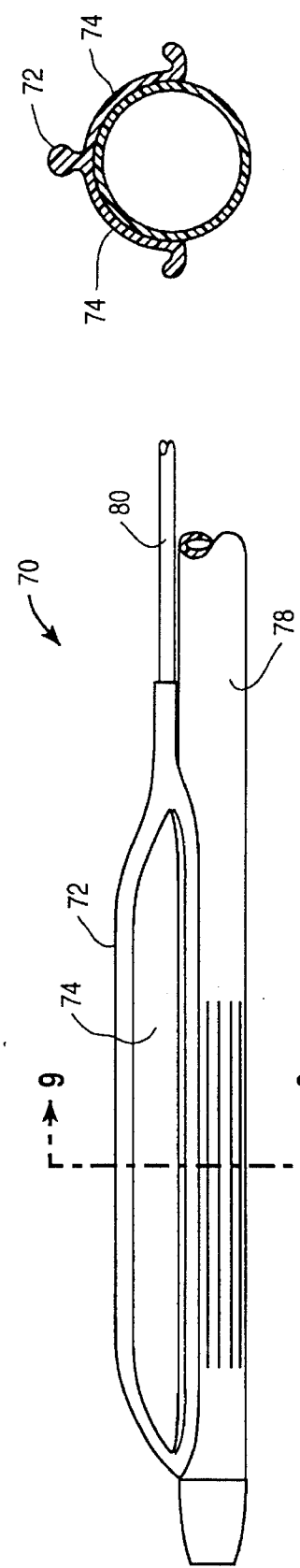

PERFUSION SHUNT DEVICE AND METHOD

CROSS-REFERENCE TO RELATED APPLICATIONS

This application is related to application Ser. No. 08/222,143, filed on Apr. 1, 1994, and is a continuation-in-part of application Ser. No. 08/221,613, filed on Apr. 1, 1994, the full disclosures of which are incorporated herein by reference.

BACKGROUND OF THE INVENTION

1. Field of the Invention

This invention relates generally to intravascular dilatation devices, and more specifically to intravascular catheters to provide blood flow during dilatation and other therapeutic and diagnostic procedures.

In percutaneous transluminal angioplasty procedures, a catheter having an expansible distal end, usually in the form of a balloon, is positioned in a lumen of a blood vessel with the distal end disposed within a stenotic atherosclerotic region of the vessel. The expansible end is then expanded to dilate the vessel and restore adequate blood flow through the diseased region. During dilatation blood flow is interrupted, limiting inflation time to between 0.5 and 3 minutes.

While angioplasty has gained wide acceptance, it continues to be limited by two major problems, abrupt closure and restenosis. Abrupt closure refers to the acute occlusion of a vessel immediately after or within the initial hours following the dilatation procedure. This complication, occurring in approximately one in twenty cases, frequently results in myocardial infarction and death if blood flow is not quickly restored. At present, arterial dissections, one of the causes of abrupt closure, are treated by prolonged balloon inflations lasting more than 5 minutes. Special angioplasty balloon catheters which allow for perfusion through the dilatation catheter during inflation are required for this purpose.

Restenosis refers to the re-narrowing of an artery after an initially successful angioplasty. Restenosis usually occurs within the initial six months after angioplasty and afflicts approximately one in three cases. Therefore, approximately one-third of treated patients will require additional revascularization procedures. Many different strategies have been tried unsuccessfully to reduce the restenosis rate, including mechanical (e.g., prolonged balloon inflations, atherectomy, laser and stenting) and pharmacologic (e.g., calcium antagonists, ace inhibitors, fish oils, steroids and anti-metabolic) approaches. One promising new strategy is to delivery agent directly to the arterial wall at the site of angioplasty. Several devices have been developed to deliver agent locally into the arterial wall. Similar to angioplasty balloon catheters, balloon deployed drug delivery catheters interrupt blood flow, limiting the time available to deliver agent.

Thus, it would be desirable to provide perfusion capabilities to angioplasty catheters and to agent delivery devices for the treatment of abrupt closure and restenosis and other purposes.

2. Description of the Background Art

A drug delivery catheter having an internal blood perfusion lumen and external drug delivery balloon is described in WO93/21985. U.S. Pat. Nos. 5,318,535; 5,308,356; 5,300,085; 5,284,473; 5,087,247; 4,892,519; and 4,790,315, describe angioplasty balloon catheters having integral blood perfusion capability. U.S. Pat. No. 4,661,094, describes a blood perfusion catheter intended primarily to provide blood flow through an occluded blood vessel. U.S. Pat. Nos. 5,163,921 and 5,180,364, describe guiding catheters having perfusion flow ports at their distal ends. Angioplasty catheters having integral blood perfusion capability are commercially available, e.g., under the tradename ACS Rx Perfusion™ Coronary Dilatation Catheter, from Advanced Cardiovascular Systems, Inc., Temecula, Calif., as described in a package insert copyright 1990.

SUMMARY OF THE INVENTION

According to the present invention, apparatus and methods are provided for establishing perfusion blood flow past an expanded balloon in a blood vessel during angioplasty and related procedures. Apparatus comprise a perfusion shunt device which includes a flexible conduit structure having one or more blood perfusion paths extending axially over at least a portion thereof. Methods comprise securing the flexible conduit structure to an expansible balloon on a vascular catheter prior to balloon expansion in the blood vessel. The flexible conduit structure is attached to the catheter at positions proximal of and distal to the expansible balloon. In particular, the flexible conduit will not be attached to the balloon structure itself. By securing the flexible conduit to the catheter only at positions proximally and distally of the balloon, balloon expansion will not be constrained by direct attachment to the flexible conduit, and the flexible conduit will be able to shift position as the balloon radially expands. Additionally, by securing the flexible conduit to the catheter at positions which lie immediately proximal of and distal to the expansible balloon, the flexible conduit will be deformed in a desirable arcuate profile which further exposes the proximal and distal ends of the flow paths to the blood vessel lumen as the balloon is expanded.

The perfusion shunt devices of the present invention comprise the flexible conduit structure, a proximal shaft structure extending proximally from the conduit structure, and means for securing the conduit structure to the catheter at locations proximal of and distal to an expansible balloon on the catheter. The blood perfusion path(s) on the flexible conduit structure may be in the form of fully-enclosed axial lumens having a plurality of spaced-apart ports to permit the inflow and outflow of blood, open axial channels which permit the inflow and outflow of blood at any location, or any other structure on or adjacent to the conduit structure which, when the balloon is expanded against the inner wall of the blood vessel, will provide a blood perfusion path(s) past the expanded balloon.

The shaft structure extends proximally from the conduit structure and may be attached directly or indirectly thereto. In a first embodiment, the shaft structure will comprise a rod, hypotube, or other small-diameter tether which is secured directly to the conduit structure. Such rods may be attached to the proximal end of the conduit structure or may optionally extend axially through the entire length of the conduit structure, and will lie parallel to the balloon catheter body in the blood vessel (typically with most of its length within a guiding catheter). Alternatively, the proximal shaft structure may comprise a tubular body which receives the vascular catheter as a sleeve, frequently being a proximal extension of the balloon-securing means, as described in more detail hereinbelow.

In some cases, the proximal shaft structure may not be needed. Clips or anchors may be provided on the flexible conduit structure so that the conduit can be mounted on a balloon catheter when the balloon is withdrawn from the blood vessel lumen, usually after an initial angioplasty procedure has been performed. An advantage of the design is the ease with which it could be post-loaded on the angioplasty balloon. No commitment to use the device need to be made at the beginning of a procedure. The need to withdraw the catheter prior to mounting of the flexible conduit, however, could be a disadvantage since the conduit structure is not immediately available for use of the treatment site.

The flexible conduit structure is attached to the vascular catheter at locations on the catheter which are proximal of and distal to the expansible balloon. The attachment means may include anchors which are proximal of and distal to the balloon and which do not encroach over (but which are not directly attached to) thee balloon in any way. Alternatively, the attachment means may comprise a variety of expansible cage structures which extend over the balloon. In the latter case, the expansible cage structures will preferably be attached to the flexible conduit structure only at positions proximal of and distal to the location which receives the balloon. In this way, the desired "free-floating" mounting of the conduit structure over the balloon is maintained.

The balloon attaching means may comprise a single anchor disposed near the distal end of the conduit structure, where the anchor captures the distal end of an angioplasty balloon catheter. Usually, at least one additional anchor will be present on the conduit structure for capturing a portion of the catheter proximally of the balloon. The distal anchor will preferably have a receptacle open in a proximal direction for receiving the distal end of the balloon catheter, where the receptacle is radially offset from the flexible conduit structure. Expansible cage structures may be in the form of axially split tubes, radially expansible meshes, elastomeric tubes, and the like. Optionally, the proximal shaft structure may be formed as a proximal extension of the expansible cage.

Methods according to the present invention comprise securing the flexible conduit structure over an expansible balloon on a vascular catheter. The conduit is anchored to the catheter only at locations distal of and proximal to the expansible balloon. In particular, the flexible conduit structure is not directly attached to the balloon. The catheter having the flexible conduit structure in place over the balloon may then be positioned at a treatment site within a blood vessel. The balloon may be expanded at the treatment site, wherein blood flows through perfusion path(s) past the expanded balloon.

Optionally, the apparatus and methods of the present invention may be modified to provide drug infusion paths, as generally described in parent application Ser. No. 08/221, 613, the full disclosure of which has previously been incorporated herein by reference. It will thus be appreciated that whenever the flexible conduit structure is described in the specification or claims, it could be modified to include drug infusion lumens, channels, or other release means. For simplicity in the following description and claims, however, no direct references will be made to drug infusion.

BRIEF DESCRIPTION OF THE DRAWINGS

FIG. 6A is an elevational view of the distal end of an alternative embodiment of a catheter constructed in accordance with the principles of the present invention, wherein the balloon attachment structure includes an elastomeric tube.

FIG. 6B is an elevational view of the distal end of a third embodiment of a catheter constructed in accordance with the principles of the present invention, wherein the balloon attachment structure comprises an expansible mesh tube.

FIG. 6C is an elevational view of the distal end of a fourth embodiment of a catheter constructed in accordance with the principles of the present invention, wherein the balloon attachment structure comprises an expansible pouch formed from a non-compliant material.

FIG. 7 is an elevational view of a fourth embodiment of a catheter constructed in accordance with the principles of the present invention, wherein the balloon attachment structure comprises a sleeve tube which is axially slit near its distal end and which extends proximally to define the proximal shaft structure of the device.

FIG. 8 is an elevational view of the distal end of a fifth embodiment of a perfusion shunt device constructed in accordance with the principles of the present invention, wherein the flexible conduit structure includes axial blood perfusion channels over its surface.

FIG. 9 is a cross-sectional view taken along line 9—9 of FIG. 8.

DESCRIPTION OF THE SPECIFIC EMBODIMENTS

Figure 1:
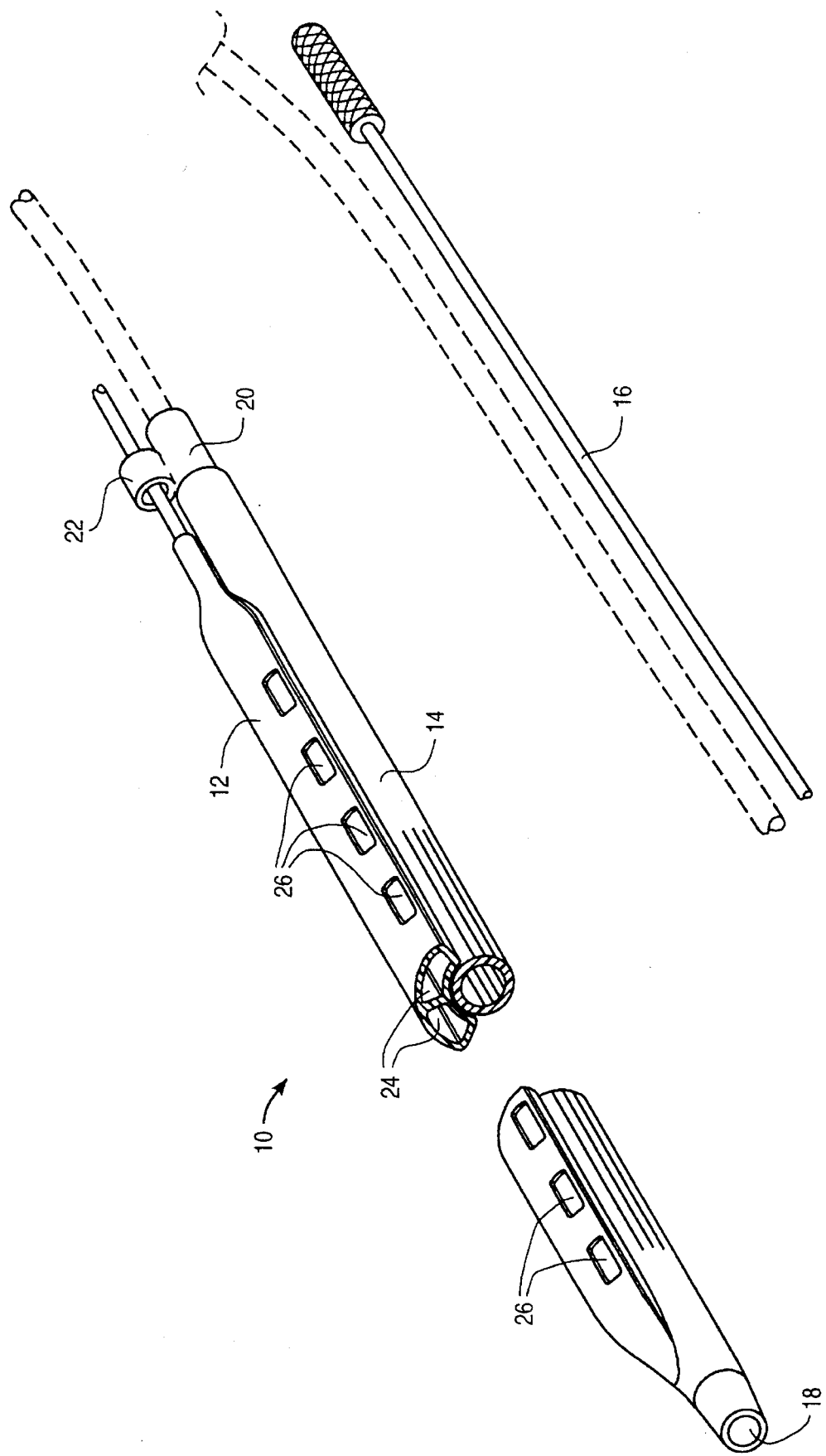
FIG. 1 is a perspective view of a perfusion shunt device constructed in accordance with the principles of the present invention and including a split-tube balloon-attachment structure and a rod-like proximal shaft structure connected directly to a flexible conduit structure.

Perfusion shunt devices according to the present invention comprise a flexible conduit structure which may be positioned over an expansible balloon, typically a dilatation balloon on a vascular angioplasty catheter. The flexible conduit structure provides at least one, and often two or more, axial perfusion paths which permit blood flow over or through the flexible conduit structure when a balloon is expanded adjacent thereto. In the absence of the flexible conduit structure, the balloon would occlude the blood vessel lumen, thus preventing blood flow.

The flexible catheter structure will have a length sufficient to extend over the entire length of the catheter balloon when expanded. Preferably, the flexible conduit structure will have a length which is greater than that of the balloon so that a proximal portion of the flexible conduit structure will lie proximal of the expanded balloon over the vascular catheter to enhance blood perfusion inlet into the flow path(s). The length of the flexible conduit structure will be sufficient to accommodate the axial perfusion paths, typically being in the range from 2.5 cm to 50 cm, preferably being from 10 cm to 40 cm, typically being from 10 cm to 30 cm.

The axial perfusion path(s) will typically extend over a length of the flexible conduit structure which can be substantially greater than that of the balloon. Most conventional angioplasty balloons are only about 1.5 cm to 5 cm in length. The perfusion flow path(s) will usually be longer, typically being at least 10 cm, usually being from 10 cm to 30 cm. Most or all of the additional length (in excess of the balloon length) will usually (although not necessarily) be on the proximal side of the balloon so that there is ample region for blood to enter the flow paths upstream of the balloon when expanded.

The axial perfusion path(s) within the flexible conduit structure may be in the form of lumens, channels, or combinations thereof, and may be aligned axially, helically, or in any other pattern that will permit blood flow from the proximal side of the balloon to the distal side. As used herein, "lumen" generally refers to an enclosed flow path within the elongate conduit structure having a plurality of axially spaced-apart ports which permit the inflow and outflow of blood. "Channel" generally refers to an open structure having at least one axially continuous aperture which permits inflow and outflow of blood at all points. In all cases, the axial perfusion paths will permit inflow of blood at locations proximal (upstream) of the expanded balloon within the blood vessel and outflow of blood at locations distal (downstream) of the expanded balloon. Additionally, the axial flow paths may provide flow from and into branch blood vessels which would otherwise be blocked by expansion of the balloon. The flow paths will preferably provide a total cross-sectional flow area of at least 0.5 mm$^2$, preferably at least 0.6 mm$^2$, and usually in the range from 0.5 mm$^2$ to 1 mm$^2$, more usually from 0.6 mm$^2$ to 0.9 mm$^2$.

The number of axial perfusion paths will depend on a number of factors. Generally, for a given total luminal cross-sectional area, fewer paths will have a lesser total resistance to flow, thus enhancing the perfusion flow rate. Alternatively, fewer paths require a smaller total luminal cross-sectional area to carry a comparable flow with an identical pressure drop. While one perfusion path would be optimum if flow area and flow resistance were the only concerns, it is also necessary to conform the path(s) to the shape of the balloon and to provide internal reinforcement web(s) in order to inhibit collapse of the paths. A particular two lumen design which provides an adequate flow area and low flow resistance while at the same time providing internal reinforcement is illustrated hereinafter.

The flexible conduit structure may be composed of a wide variety of biologically compatible materials, typically being formed from natural of synthetic polymers, such as polyvinylchloride, polyurethanes, polyesters, polyethylenes, polytetrafluoroethylenes (PTFE's), and nylons. The flexible conduit structure will usually be non-compliant, and may optionally be reinforced to maintain patency of the flow paths during use. It will be appreciated that expansion of an adjacent balloon within the blood vessel will tend to collapse lumens, channels, and other flow paths within the flexible conduit structure. To maintain patency, reinforcement layers may be incorporated within the body in order to enhance strength, toughness, and the like. Exemplary reinforcement layers include metal fiber braid, polymeric fiber braid and the like. Optionally, the flexible conduit structure may be reinforced by closed inflation lumens, as described in parent application Ser. No. 08/221,613, the full disclosure of which has previously been incorporated herein by reference, which are statically inflated to selectively strengthen the perfusion flow paths.

The flexible conduit structure will normally be formed by conventional extrusion of the desired polymeric material, forming one or more lumens, channels, or other perfusion path(s), as described in more detail hereinbelow. The cross-sectional areas and geometries of the perfusion path(s) within the conduit structure can be modified, if desired, by heat expansion and shrinkage using conventional techniques. Specific techniques for forming the conduit structures of the present invention are well-described in the patent and medical literature.

The flexible conduit structure will be removably attached to the expansible balloon of a conventional vascular balloon catheter in such a way that the axial perfusion path(s) will extend over the balloon when the balloon is expanded within the lumen of a blood vessel. Conventional balloon catheters are available from a number of commercial suppliers, such as Advanced Cardiovascular Systems, SciMed, C. R. Bard, Cordis, and others. Attachment of the flexible conduit structure to the balloon catheters will be such that the conduit structure is secured to the catheter only at locations proximal of and distal to the balloon. The flexible conduit structure will thus be free to shift position relative to the balloon as the balloon is radially expanded. Such freedom of motion provides a number of advantages. In particular, the freedom of relative movement lessens constriction and distortion of the conduit structure and the balloon. Additionally, the lack of direct attachment to the balloon combined with direct attachment to the catheter proximal to and distal of the balloon assures that the conduit structure will have a smooth, arcuate shape at both the proximal inlet and distal outlet of the flow paths. In some cases, the flexible conduit structure will be axially slidably attached to the underlying balloon catheter, particularly at location(s) proximal to the balloon (when the distal attachment points are axially fixed). Such an arrangement advantageously prevents the flexible conduit from disengaging at the distal attachment point (i.e., it cannot slide out of engagement), while permitting some axial movement at the proximal attachment locations(s) which enhances the ability of the conduit structure to conform to the underlying balloon in a smooth arc or curve.

Exemplary attachment structures include discrete anchors which are spaced-apart on opposite sides of the balloon, as well as expansible cage structures which are disposed directly over the balloon (but which are connected to the flexible conduit structure only at locations proximal of and distal to the region which receives the balloon). Such attachment structures are described in detail hereinbelow in connection with the figures.

A proximal shaft structure will usually be connected directly or indirectly to the flexible conduit structure (although in some designs it will be possible to secure the flexible conduit over a balloon without providing any proximal structure attached to the conduit). The shaft structure is preferred to permit manipulation of the flexible conduit structure by the treating physician. Thus, the proximal shaft structure will be sufficiently long to extend from the conduit structure over the entire length of the balloon catheter and outward through the introducer sheath so that it can be accessible. In a first embodiment, the shaft structure is a narrow-diameter rod or hypotube, typically having a diameter below 1 mm, preferably below 0.8 mm usually between 0.8 mm and 0.7 mm for hypotube and between 0.6 mm and 0.4 mm for a rod structure. The rod may be attached directly to the flexible conduit structure and will be disposed parallel to the proximal body of the balloon catheter which extends outward through the vasculature. In the embodiment illustrated hereinafter, the proximal shaft will be secured to the proximal end of the flexible conduit. In many cases (not illustrated) it may be preferred to extend the shaft structure axially through the entire flexible conduit structure, typically through a dedicated lumen, in order to enhance the attachment.

Alternatively, the proximal shaft structure may comprise a tubular body which is formed continuously with the balloon-securing structure. For example, the shaft and balloon-securing structure may form a continuous tube, wherein a distal portion of the tube is axially split to permit balloon expansion therein. Thus, the shaft is in the form of a sleeve having a flexible conduit structure attached over a distal portion thereof. Alternatively, the tube can include an elastomeric region, mesh structure, enlarged (non-distensible) pouch, or the like, each of which permit internal balloon expansion.

Referring now to FIG. 1, a first embodiment of the perfusion shunt device of the present invention will be described. The perfusion shunt device 10 comprises a flexible conduit structure 12, a balloon-securing sleeve 14, and a proximal shaft 16. The balloon-securing sleeve 14 has an open port 18 at its distal end and a shaft anchor structure 20 at its proximal end. The proximal shaft 16, which is in the form of a narrow-diameter rod or hypotube, is secured directly to the proximal end of the flexible conduit structure 12 and passes through a ring structure 22 on the anchor 20.

The flexible conduit structure 12 comprises a pair of lumens 24 extending axially from its distal end to proximal end. Each lumen 24 includes a plurality of axially spaced-apart blood perfusion ports 26. The construction of such a dual-lumen flexible conduit structure (which is formed integrally with an underlying balloon-containment sleeve, in contrast to the present invention) is described in more detail in copending application Ser. No. 08/222,143, the full disclosure of which has been previously incorporated herein by reference.

Figure 2:
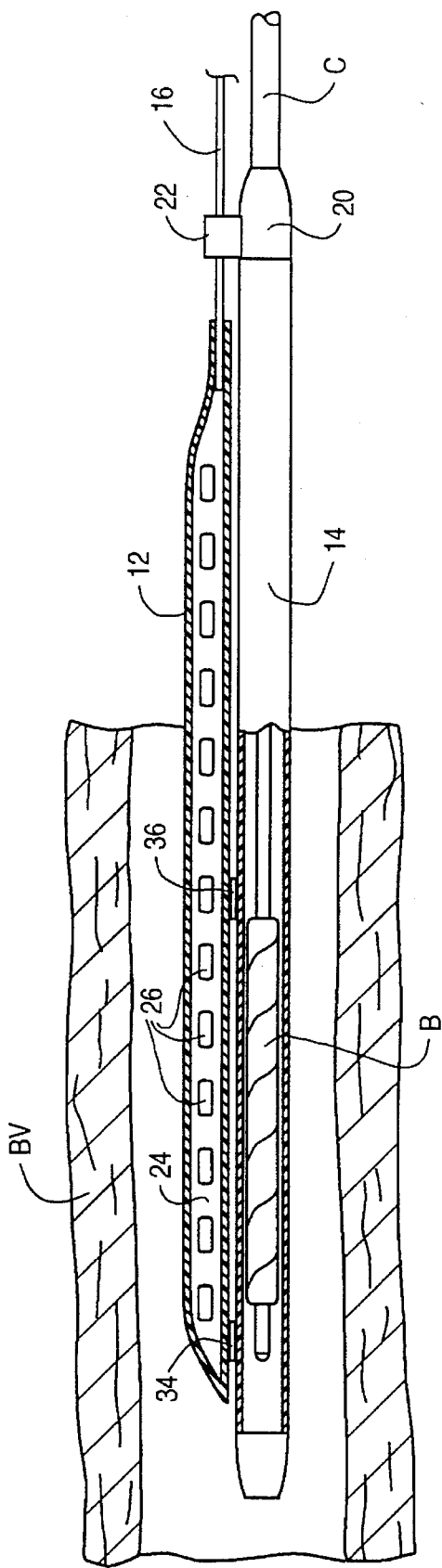
FIG. 2 is an elevational view of a distal portion of the perfusion shunt device of FIG. 1 shown in a blood vessel over a non-expanded balloon.
Figure 3:
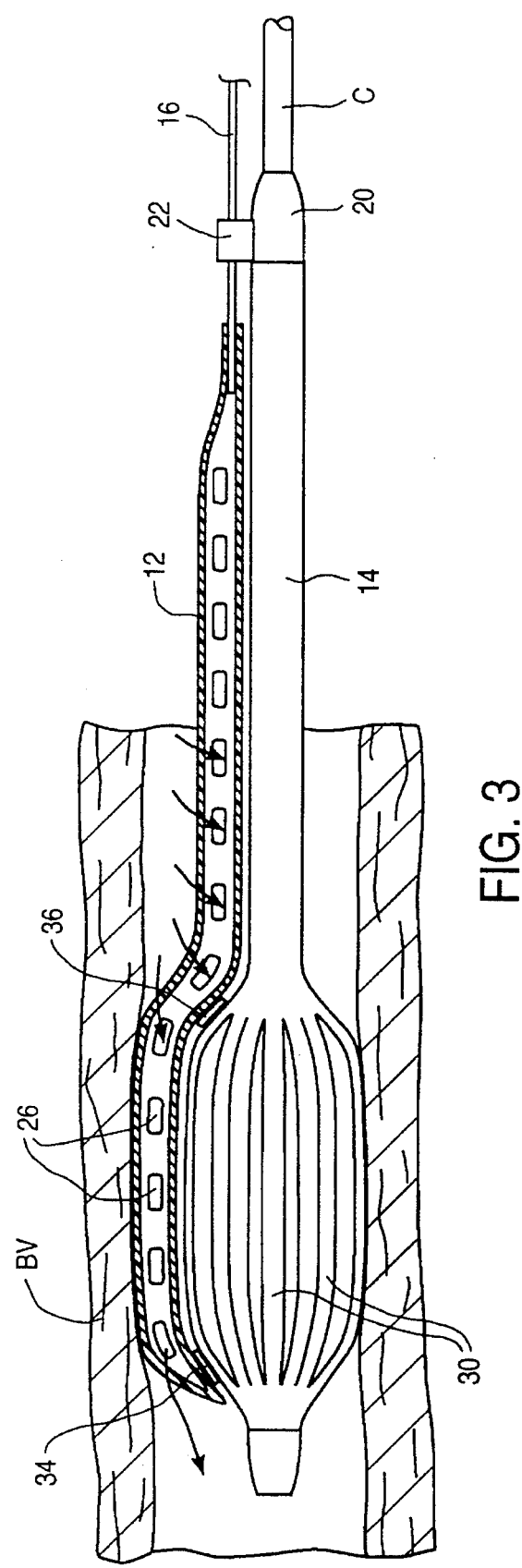
FIG. 3 is a view similar to FIG. 2, except that the balloon is expanded to engage the flexible conduit structure against the interior wall of the blood vessel.
Figure 5:
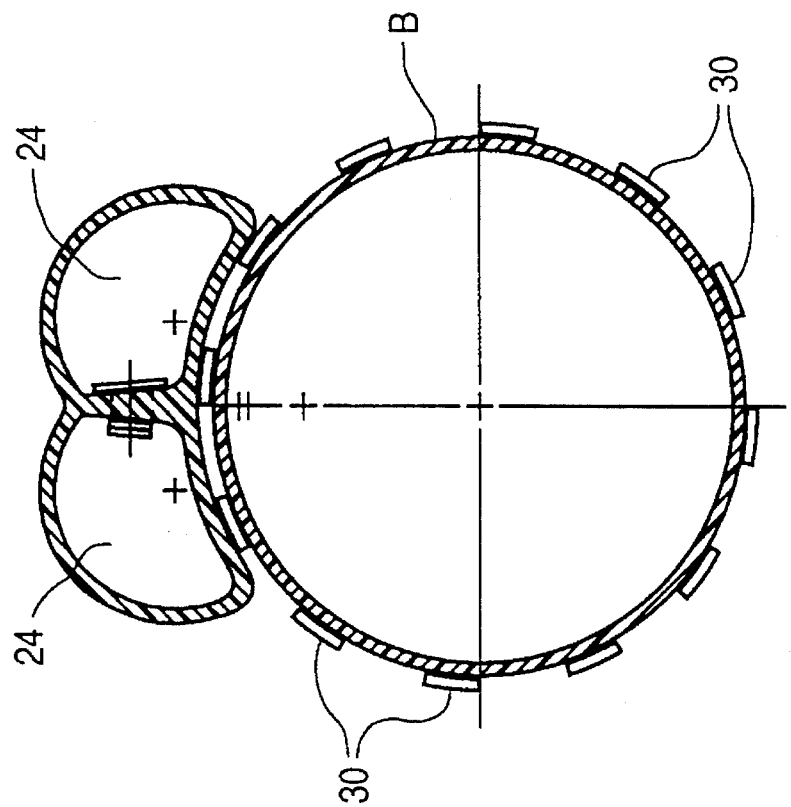
FIG. 5 is a view similar to FIG. 4, shown with an expanded balloon therein.
Figure 4:
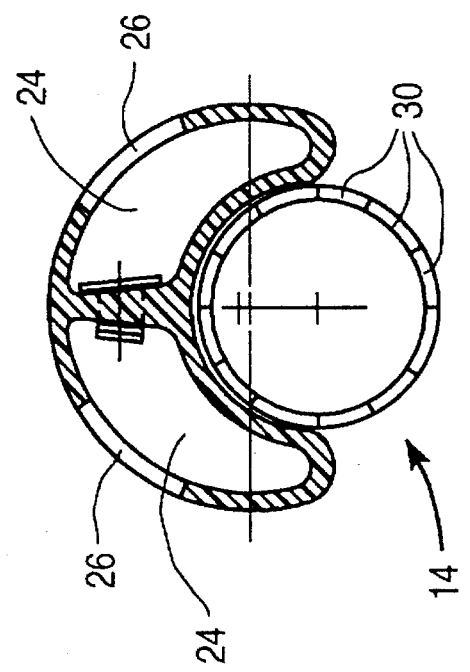
FIG. 4 is a cross-sectional view of the catheter of FIG. 1, shown in a non-expanded configuration.
Figure 10:
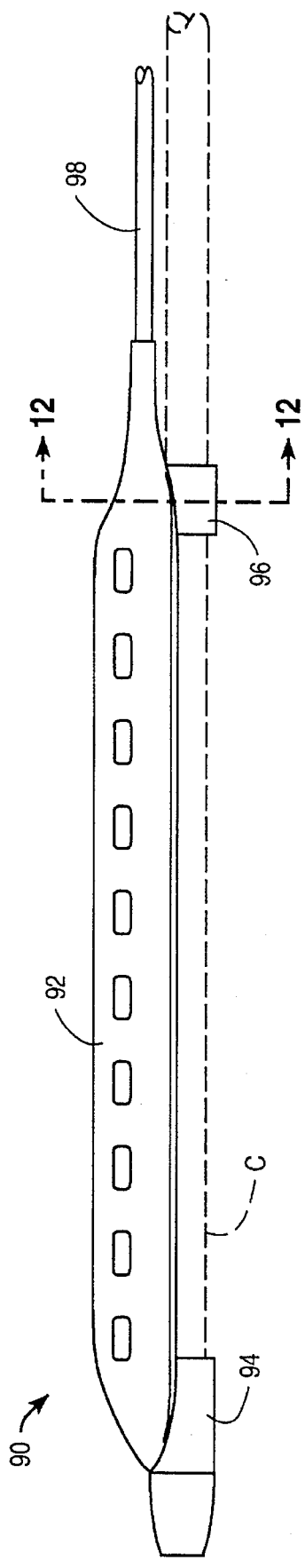
FIG. 10 is an elevational view of the distal end of a sixth embodiment of a perfusion shunt device constructed in accordance with the principles of the present invention, wherein the balloon attachment structure consists of proximal and distal anchors which are secured over a balloon catheter.
Figure 12:
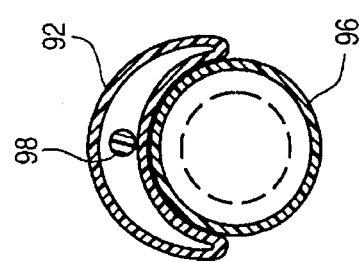
FIG. 12 is a cross-sectional view taken along line 12—12 of FIG. 10.

Referring now to FIGS. 1–5, the balloon-securing sleeve 14 is axially split into a number of discrete segments 30, as best observed in FIGS. 4 and 5. The axially split region of the sleeve 14 will be sufficiently long to accommodate a conventional balloon Bona balloon angioplasty catheter C (FIG. 2). The balloon-securing sleeve 14 and flexible conduit structure 12 are separate, discrete components which are attached to each other only at attachment points 34 and 36 (FIGS. 2 and 3), which are disposed distally of and proximally to the balloon-receiving region sleeve 14, respectively. Thus, when the balloon B is expanded within the sleeve 14, as illustrated in FIG. 3, the distal and proximal regions of the sleeve 14 over the balloon will be formed into smooth curves, as illustrated. Such smooth curves help to expose the ports 26 upstream and downstream of the balloon to blood flowing closer to the center of the blood vessel being treated.

Referring now to FIG. 6A, a perfusion shunt device 40, similar in most respects to device 10, is illustrated. The device 40 is identical, except that an elastomeric segment 42 is provided in place of the axially split portion of sleeve 14'. All other numbering in FIG. 6A is identical to that used in FIGS. 1–5.

Another perfusion shunt device 44 having a radially expansible mesh section 46 in sleeve 14" is illustrated in FIG. 6B. All other details of construction of device 44 may be identical to those described for FIG. 1. Thus, all other reference numbers used for identifying like components are identical.

Yet another perfusion shunt device 45 having a radially expansible pouch 47 formed from a non-compliant material, such as polyethyleneterephthalate (PET), is illustrated in FIG. 6C. The pouch 47 will be folded (as illustrated in FIG. 6C) prior to internal expansion of a balloon. The pouch 47 will usually be sized smaller than the balloon with which it is to be used so that the pouch will constrain radial expansion of the balloon. In that way, the same balloon which has been used in an angioplasty procedure may be reused in the subsequent perfusion procedure with minimum risk of over stretching the blood vessel. It will be appreciated that presence of the flexible conduit 12 over the balloon could increase the effective balloon diameter to some extent. Should an increase in effective balloon diameter be desired, the balloon can be further inflated to distend the pouch and provide the desired enlargement.

Referring now to FIG. 7, yet another embodiment of the perfusion shunt device of the present invention will be described. Perfusion shunt device 50 includes a flexible conduit structure 52 which is analogous to structure 12 in FIG. 1. The flexible conduit structure 52, however, is not attached to a proximal shaft. Instead, perfusion shunt device 50 employs an elongate sleeve 54 which acts as both a balloon-securing sleeve and a proximal shaft structure. A balloon-securing region 56 within the sleeve 54 may comprise an axially slit region (wherein the sleeve may be composed of a non-elastomeric material) as illustrated, or may comprise any of the other balloon containment cages described previously. A conventional balloon catheter C (shown in broken line) is received within a lumen 58 of the sleeve 54 which extends the entire distance from the distal port 60 to a proximal housing 62 of the device. It will be appreciated that the flexible conduit structure 52 is attached to the sleeve 54 only at locations distal to and proximal of the expansible region 56 of sleeve 54 which receives the balloon on catheter C.

Referring now to FIGS. 8 and 9, yet another embodiment of the perfusion device shunt device will be described. Perfusion shunt device 70 is similar in most respects to device 10 of FIGS. 1–5, except that the flexible conduit structure 72 provides open, axial channels 74 in place of the closed lumens 24 in the conduit structure 12. Balloon-securing sleeve 78 and axial rod 80 may be formed substantially identical to the corresponding components in device 10.

Figure 11:
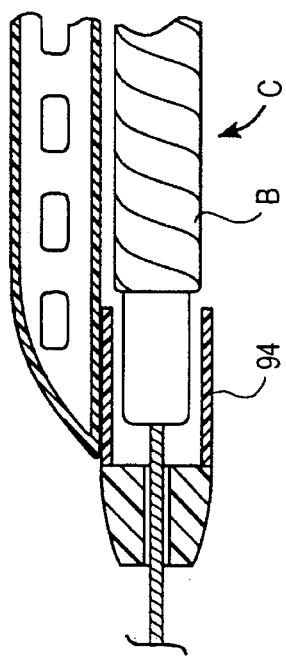
FIG. 11 is a detailed view of the distal tip of the device of FIG. 10, shown in section with an uninflated balloon catheter in place.

Referring now to FIGS. 10–13, still another embodiment of the perfusion shunt device of the present invention will be described. Perfusion shunt device 90 comprises a flexible catheter structure 92 which is similar in most respects to structure 12 of FIG. 1. Device 90, however, does not employ an expansible cage or sleeve structure, as with all previous embodiments. Instead, device 92 employs discrete distal anchor 94, which receives the distal end of a balloon catheter C, as best seen in FIG. 11. Preferably, device 90 further comprises proximal anchor structure 96, which is located near the proximal end of the conduit structure 92. A proximal rod 98 is attached directly to the conduit structure 92.

Figure 13:
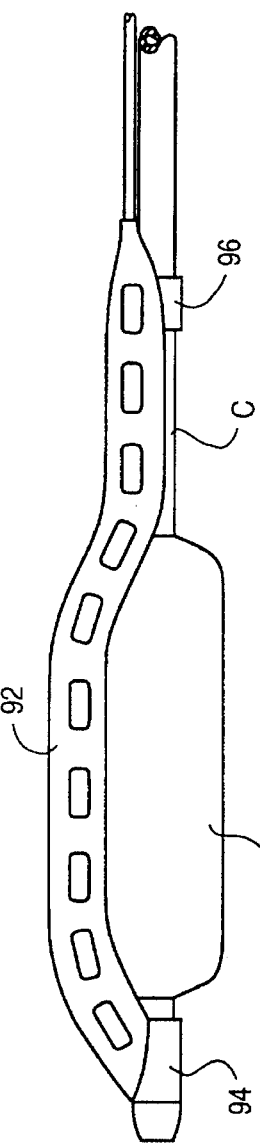
FIG. 13 illustrates the device of FIG. 10 when in place over an inflated balloon.

In use, the perfusion shunt device 90 will be attached over balloon B of the catheter C, with proximal anchor 96 at a location proximally spaced-apart from the balloon. The balloon B is inflated, as illustrated in FIG. 13, with the desired arcuate profiles of the conduit structure 92 being achieved.

Any of the perfusion shunt devices described herein may be used by loading them onto a balloon catheter so that the flexible conduit structure lies over the balloon while the catheter is outside the body. Indeed, the device 90 of FIGS. 10–13 and the device which does not include a proximal shaft structure (not illustrated) must be loaded on the catheter outside the body. The other embodiments must be loaded over the distal end of the balloon catheter while the balloon catheter is outside the body. The other embodiments, however, permit the flexible conduit structure to be distally advanced and proximally withdrawn relative to balloon of the balloon catheter while the catheter and the shunt device both remain within the blood vessel, which ability is not available with device 90.

Although the foregoing invention has been described in some detail by way of illustration and example, for purposes of clarity of understanding, it will be obvious that certain changes and modifications may be practiced within the scope of the appended claims.

What is claimed is:

1. A perfusion shunt device comprising:
   a flexible conduit structure having a proximal end, a distal end, and a blood perfusion path extending axially over at least a portion of the conduit structure;
   a proximal shaft structure extending proximally from the conduit structure; and
   means attached to the conduit structure for securing the conduit structure to a catheter at locations proximal of and distal to an expansible balloon on the catheter, wherein the flexible conduit structure is not directly secured over the balloon.

2. A device as in claim 1, wherein the blood perfusion path comprises at least one lumen extending through the conduit structure, wherein the lumen has a plurality of axially spaced-apart ports which permit blood perfusion into the out of the lumen.

3. A device as in claim 2, wherein the blood perfusion path comprises a pair of axial lumens, each of which has a plurality of axially spaced-apart ports.

4. A device as in claim 1, wherein the blood perfusion path comprises at least one axial channel formed in an exterior surface of the conduit structure.

5. A device as in claim 1, wherein the shaft structure comprises a rod attached directly to the proximal end of the flexible conduit structure.

6. A device as in claim 1, wherein the shaft structure comprises a tubular sleeve having a proximal end and a distal end.

7. A device as in claim 6, wherein a distal portion of the tubular sleeve is axially split to allow for radial expansion and comprises the balloon-securing means.

8. A device as in claim 1, wherein the balloon-attaching means comprises an anchor disposed near the distal end of the conduit structure, which anchor captures a distal end of an angioplasty balloon catheter.

9. A device as in claim 8, wherein the single anchor is a distal end piece having a receptacle open in a proximal direction for receiving the distal end of the angioplasty balloon catheter, wherein said receptacle is radially offset from the flexible conduit structure.

10. A device as in claim 8, wherein the conduit-securing means comprises at least one additional anchor disposed on the conduit structure, which additional anchor(s) capture the angioplasty balloon catheter proximally of the balloon.

11. A device as in claim 1, wherein the conduit-securing means comprises an expansible cage which receives the balloon and which is attached to the flexible conduit structure only at locations distal and proximal to a portion of the cage which receives the balloon.

12. A device as in claim 11, wherein the expansible cage comprises an axially split tube.

13. A device as in claim 11, wherein the expansible cage comprises an elastomeric tube.

14. A device as in claim 11, wherein the expansible cage comprises a mesh structure.

15. A device as in claim 11, wherein the expansible cage comprises a pouch composed of a non-compliant material.

16. A device as in claim 11, wherein a proximal extension of the expansible cage comprises the shaft.

17. A method for perfusing blood past a treatment site within a blood vessel, said method comprising:
   providing a flexible conduit structure having a blood perfusion path extending axially over at least a portion thereof;
   positioning the flexible conduit over an expansible balloon on a vascular catheter, wherein the conduit is attached to the catheter at locations distal of an proximal to the expansible balloon but is not directly attached to the balloon; and
   expanding the balloon at the treatment site within the blood vessel, wherein blood flows through the perfusion path past the expanded balloon.

18. A method as in claim 17, wherein the flexible conduit is attached by a first anchor disposed at a distal end of the flexible conduit which is placed over a distal end of the balloon catheter and at least one additional anchor which is placed over a proximal portion of the catheter.

19. A method as in claim 17, wherein the flexible conduit is attached by an expansible cage which receives the expansible balloon and which is attached to the flexible conduit structure only at locations distal and proximal to a portion of the cage which receives the balloon.

20. A method as in claim 17, wherein flexible conduit is positioned over the expansible balloon while the vascular catheter is withdrawn from the blood vessel.

21. A method as in claim 17, wherein the flexible conduit is positioned over the expansible balloon while the vascular catheter is disposed within the blood vessel.

* * * * *